United States Patent
De Lemos et al.

(10) Patent No.: US 10,137,073 B2
(45) Date of Patent: Nov. 27, 2018

(54) COSMETIC COMPOSITIONS COMPRISING CERAMIDES AND CHOLESTEROL

(71) Applicant: L'OREAL, Paris (FR)

(72) Inventors: Joyce Ann De Lemos, Brooklyn, NY (US); Patricia Brieva, Manalapan, NJ (US); Donna McCann, Oxford, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/986,662

(22) Filed: Jan. 2, 2016

(65) Prior Publication Data
US 2017/0189297 A1   Jul. 6, 2017

(51) Int. Cl.
| | | |
|---|---|---|
| *A61K 8/63* | (2006.01) | |
| *A61K 8/06* | (2006.01) | |
| *A61K 8/42* | (2006.01) | |
| *A61K 8/49* | (2006.01) | |
| *A61K 8/81* | (2006.01) | |
| *A61K 8/891* | (2006.01) | |
| *A61K 8/92* | (2006.01) | |
| *A61Q 19/00* | (2006.01) | |
| *A61Q 19/08* | (2006.01) | |
| *A61K 8/68* | (2006.01) | |

(52) U.S. Cl.
CPC ............... *A61K 8/63* (2013.01); *A61K 8/064* (2013.01); *A61K 8/42* (2013.01); *A61K 8/494* (2013.01); *A61K 8/4953* (2013.01); *A61K 8/68* (2013.01); *A61K 8/8111* (2013.01); *A61K 8/891* (2013.01); *A61K 8/922* (2013.01); *A61Q 19/00* (2013.01); *A61Q 19/007* (2013.01); *A61Q 19/08* (2013.01); *A61K 2800/48* (2013.01); *A61K 2800/49* (2013.01); *A61K 2800/596* (2013.01); *A61K 2800/70* (2013.01)

(58) Field of Classification Search
CPC ....................................................... A61K 8/68
See application file for complete search history.

(56) References Cited

U.S. PATENT DOCUMENTS

| | | | | |
|---|---|---|---|---|
| 5,041,281 | A * | 8/1991 | Strobridge | A61K 8/06 424/59 |
| 8,147,883 | B1 | 4/2012 | Msika et al. | |
| 8,313,755 | B2 | 11/2012 | Shiroyama et al. | |
| 8,486,463 | B1 * | 7/2013 | Brieva | A61K 8/97 424/725 |
| 8,710,034 | B2 | 4/2014 | Maes et al. | |
| 8,758,736 | B2 | 6/2014 | Lorant | |
| 9,161,896 | B2 | 10/2015 | Yamamoto | |
| 9,193,852 | B2 | 11/2015 | Goldberg et al. | |
| 9,295,621 | B2 * | 3/2016 | Maes | A61K 8/06 |
| 2004/0009213 | A1 * | 1/2004 | Skold | A61K 8/42 424/449 |
| 2005/0152865 | A1 | 7/2005 | Yamamoto et al. | |
| 2007/0082042 | A1 | 4/2007 | Park et al. | |
| 2007/0286835 | A1 * | 12/2007 | Park | A61K 8/042 424/70.22 |
| 2010/0184733 | A1 * | 7/2010 | Korevaar | A61K 8/361 514/171 |
| 2014/0170251 | A1 | 6/2014 | Trumbore et al. | |
| 2014/0335137 | A1 | 11/2014 | Hayes | |
| 2015/0118334 | A1 | 4/2015 | Rozenblat | |
| 2015/0335556 | A1 | 11/2015 | Roudot et al. | |

OTHER PUBLICATIONS

Linden, J., "Adenosine in Tissue Protection and Tissue Regeneration", Mol. Pharmacol. 2005, vol. 67, No. 5, pp. 1385-1387.
Machado, M. et al., "New cosmetic emulsions for dry skin." J. Cosmetic Dermatology. 2007, vol. 6, pp. 239-242.
PCT Notification of Transmittal of the International Search Report and the Written Opinion of the International Searching Authority, or the Declaration, issued in International Application No. PCT/US16/68218.

* cited by examiner

*Primary Examiner* — Kyle A Purdy
(74) *Attorney, Agent, or Firm* — Polsinelli PC

(57) ABSTRACT

The present disclosure relates to cosmetic compositions, typically in the form of an emulsion, comprising cholesterol, at least one ceramide, and oils. The compositions are particularly useful for supporting natural lipid barrier function of skin. Furthermore, the compositions treat skin dryness, skin damage, and the appearance of wrinkles, dark spots, and uneven skin texture. Also disclosed is a process for manufacturing the cosmetic compositions.

12 Claims, No Drawings

COSMETIC COMPOSITIONS COMPRISING CERAMIDES AND CHOLESTEROL

FIELD OF THE DISCLOSURE

The present disclosure relates to cosmetic compositions, typically in the form of an emulsion, comprising cholesterol, at least one ceramide, and oil. The compositions are particularly useful for supporting natural lipid barrier function of skin. The compositions also treat skin dryness, help repair skin damage, and eliminate the appearance of wrinkles, dark spots, and uneven skin texture.

BACKGROUND

Skin acts as a natural barrier between internal and external environments and therefore plays an important role in vital biological functions such as protection against mechanical and chemical injury, micro-organisms, and ultraviolet damage. The health and appearance of skin, however, can deteriorate due to environmental factors, genetic makeup, nutrition, and sun exposure. With aging, the outer skin layer (epidermis) thins, even though the number of cell layers remains unchanged. The number of pigment-containing cells (melanocytes), however, decreases. Therefore, the skin appears pale and translucent. Large pigmented spots (age spots, liver spots, or lentigos) may appear in sun-exposed areas. Changes in the connective tissue reduce the skin's strength and elasticity. This is known as elastosis. It is more noticeable in sun-exposed areas (solar elastosis). Elastosis produces the leathery, weather-beaten appearance common to farmers, sailors, and others who spend a large amount of time outdoors. Dehydration increases the risk of skin injury. Poor nutrition can also negatively impact the skin, causing dryness, rash, and puffiness.

Ceramides are a group of natural waxy, fatty substances in the skin, composed of sphingosine and lipids (fatty acids) bonded together. Ceramides make up about 50% of all skin lipids and are manufactured in the lower, living cells of the epidermis. As the cells mature and move to the surface, ceramides are released to the topmost layer, the stratum corneum. In the stratum corneum layer, ceramides combine with cholesterol (another important lipid found in the skin) and fatty acids to form an ordered, tightly-packed, layered, sheet-like arrangement between the dead cells. Ceramides and cholesterol protect against moisture loss to keep skin youthful and supple, and support the skin's matrix, keeping it firm. Young individuals manufacture ample ceramides and cholesterol to keep the skin healthy. However, with age, production declines, and skin begins to sag and wrinkle.

SUMMARY OF THE DISCLOSURE

The present disclosure relates to cosmetic compositions, typically in the form of an emulsion, comprising cholesterol, at least one ceramide, and oil. The compositions are particularly useful for supporting the natural lipid barrier function of skin. Furthermore, the compositions treat skin dryness, help in repairing skin damage due to photoaging (or other environmental stress), and eliminate the appearance of wrinkles, dark spots, and uneven skin texture. The compositions are unique in that they include high amounts of both ceramides and cholesterol—higher amounts than have previously been incorporated into stable commercial products. Additionally, the compositions are distinctive because cholesterol is the dominant lipid component instead of ceramides (or other types of lipids).

The cosmetic compositions comprise:
(a) cholesterol;
(b) one or more ceramides;
(c) one or more oils;
(d) one or more emulsifiers; and
(e) one or more thickeners.

The composition may be in the form of a liquid emulsion, such as a liquid-lotion, liquid-gel, liquid-cream, or a cream emulsion, such as a thick cream or gel-cream, foam or mousse wherein the liquid emulsion form has a thinner consistency than the cream emulsion form.

In some instances, the amount of cholesterol in the composition is from 1 wt. % to 10 wt. % and the amount of ceramides in the composition is from 0.1 wt. % to 5 wt. %. The (b) one or more ceramides may include, for example, both ceramide-3 and ceramide-EOP. Typically, the ratio of the (a) cholesterol to the (b) one or more ceramides is at least 1.1:1.0 to 10:1.0. The one or more oils may include, for example, hydrogen-based oils and/or silicone oils. Organosiloxane emulsifiers and thickeners such as sodium polyacrylate and ammonium polyacryloyldimethyl taurate may also be included in the compositions.

The present disclosure further relates to various methods for supporting natural lipid barrier function of skin comprising applying the cosmetic compositions described herein to the skin. The cosmetic compositions may additionally be used for treating skin dryness, repairing skin damage due to photoaging, and diminishing the appearance of wrinkles, dark spots, and uneven skin texture.

Finally, the present disclosure relates to methods for manufacturing the cosmetic compositions described herein. The process typically includes forming a fatty phase and a separate aqueous phase, heating both phases to a temperature of 60° C. or higher, and combining both phases to form an emulsion while maintaining both phases at a temperature of 60° C. or higher. The emulsion is then cooled to ambient temperature. Typically, the fatty phase includes the (a) cholesterol; (b), one or more ceramides; (c) one or more oils; (d) one or more emulsifiers; and (e) one more thickeners. Emulsifiers and thickeners may also be included in the aqueous phase or added during the emulsification process or even after the emulsification process. In addition to water, the aqueous phase may include, for example, one or more active ingredients. Active ingredient may be, for example, adenosine, HEPES, and/or hyaluronic acid.

DETAILED DESCRIPTION OF THE DISCLOSURE

The cosmetic compositions of the present disclosure include: (a) cholesterol; (b) one or more ceramides; (c) one or more oils; (d) one or more emulsifiers; and (e) one or more thickeners. The compositions may also include (f) one or more active ingredients. The components of the composition can be combined to form an emulsion, including, for example oil-in-water (O/W), water-in-oil (W/O), and oil-in-alcohol emulsions. In some cases the composition is a water-in-oil (W/O) emulsion.

In some cases the cosmetic composition includes 1 wt. % to 10 wt. %, 2 wt. % to 8 wt. %, 3 wt. % to 6 wt. %, or about 4 wt. % of cholesterol. The total amount of the one or more ceramides is 0.1 wt. % to 5 wt. %, 0.5 wt. % to 5 wt. %, 1 wt. % to 5 wt. %, 1 wt. % to 4 wt. %, 1 wt. % to 3 wt. %, or about 2 wt. %. The one or more ceramides in the composition may include at least ceramide-3, and may also include ceramide-EOP. The ceramide-3 may be present in a greater amount than ceramide-EOP and/or the other ceramides in the compositions. For example, ceramide-3 (or any other individual ceramide) may be present in an amount of from 0.3 wt. % to 4.0 wt. %, 0.5 wt. % to 4.0 wt. %, 0.5 wt. % to 3.0 wt. %, or from 1 wt. % to 4 wt. %. A second ceramide, such as ceramide-EOP may be present in an amount of 10 ppm to 1.0 wt. % (10,000 ppm), 10 ppm to 0.5 wt. % (5,000 ppm), or 10 ppm to 1,000 ppm.

In some embodiments, the amount of cholesterol in the composition is greater than the total amount of ceramides in the compositions, for example the ratio of cholesterol to total amount of ceramides may be from 1.1:1.0 to 10:1.0, 1.5:1.0 to 5:1, or 1.8:1 to 3:1.

In some embodiments, the total amount of the combination of cholesterol and the one or more ceramides is 1.3 wt. % to 15 wt. %, 1.5 wt. % to 15 wt. %, 2 wt. % to 12 wt. %, 2 wt. % to 10 wt. %, 3 wt. % to 9 wt. %, 4 wt. % to 9 wt. %, 4 wt. % to 8 wt. %, 5 wt. % to 7 wt. %, or about 6 wt. %.

As mentioned above, the compositions are unique in that they include high amounts of both ceramides and cholesterol, higher amounts than have previously been incorporated into stable commercial products. Also, the compositions are distinctive because cholesterol is the dominant lipid component instead of ceramides (or other types of lipids). This is achieved by separately heating a fatty phase and an aqueous phase before emulsification to prevent recrystallization of the one or more ceramides. Also, water soluble emulsifiers that are typically added to an aqueous phase (because they are water soluble), or added post-emulsification, are added to the fatty phase before emulsification. A combination of emulsifiers is used to stabilize and maintain the high levels of ceramides and cholesterol in the composition.

The composition typically includes a fatty phase and an aqueous phase. One or more oils are usually associated with the fatty phase. The amount of oil in the composition can vary, and may be from 20 wt. % to 80 wt. %, 30 wt. % to 70 wt. %, or from 40 wt. % to 60 wt. %. In some cases, the one or more oils include one or more silicone oils and/or one or more hydrocarbon based oils, for example, the compositions may include dimethicone and/or hydrogenated polyisobutene. To combine the fatty phase and the aqueous phase, emulsifiers are typically used. For examples organosiloxane emulsifiers such as lauryl PEG-9 polydimethylsiloxyethyl dimethicone and PEG/PPG-18/18 dimethicone (in dimethicone) are useful. The amount of emulsifiers in the composition typically are in an amount of 0.1 wt. % to 30 wt. %, 0.1 wt. % to 20 wt. %, 0.5 wt. % to 20 wt. %, 1 wt. % to 20 wt. %, 1 wt. % to 15 wt. %, or 1 wt. % to 10 wt. %; or from 0.5, 0.6, 0.7, 0.8, 0.9 or 1.0 wt. % to 5, 6, 7, 8, 9, or 10 wt. %.

The compositions disclosed herein may include one or more thickeners. Often more than one thickener may be used to achieve a particular consistency. In some cases, thickeners such as ammonium polyacryloyldimethyl taurate and/or sodium polyacrlate can be useful. The amount of thickeners can vary depending on the desired consistency of the final product. The thickeners may be in an amount of 0.1 wt. % to 20 wt. %, 0.1 to 10 wt. %, 0.1 wt. % to 9 wt. %, 0.2 wt. % to 9 wt. %, 0.3 wt. % to 9 wt. %, 0.4 wt. % to 8 wt. %, 0.5 wt. % to 5 wt. %, 1 wt. % to 5 wt. %, or 2 wt. % to 4 wt. %. Further, the amount of thickener may be from 0.1, 0.2, 0.3, 0.4, 0.5, 0.6, 0.7, 0.8, 0.9, 1.0, or 1.5 wt. % to 2, 3, 4, 5, 6, 7, 8, 9, 10, 15, or 20 wt. %.

The compositions may also include an active ingredient (an ingredient other than cholesterol, ceramides, oils, emulsifiers, and thickeners, which may themselves be an active ingredient that imparts beneficial characteristics to the skin). For instance the active ingredient may be a humectant and moisturizing ingredient, an anti-aging agent, a depigmenting agent, an anti-wrinkle agent, or an agent that treats oily skin. In some embodiments, adenosine is used as at least one of the active ingredients. The compositions may include 10 ppm to 10 wt. % (100,000 ppm), 10 ppm to 5 wt. % (50,000 ppm), 10 ppm to 2.5 wt. % (25,000 ppm), 10 ppm to 1 wt. % (10,000 ppm), 10 ppm to 0.5 wt. % (5,000 ppm), 10 ppm to 0.1 wt. % (1,000 ppm), or 10 ppm to 500 ppm of one or more active ingredients. In some cases, the one or more active ingredients is present in an amount from 10, 20, 30, 40, 50, 60, 70, 80, 90, 100, 150, or 200 ppm to 500, 600, 700, 800, 900, 0.1 wt. % (1000 ppm), 0.5 wt. % (5,000 ppm), 1 wt. % (10,000 ppm)), 5 wt. % (50,000 ppm), or 10 wt. % (100,000 ppm).

The compositions of the instant disclosure may be in the form of a liquid emulsion, such as a liquid-lotion, liquid-gel, liquid-cream, or a cream emulsion, such as a thick cream or gel-cream, or a foam or mousse wherein the liquid emulsion form has a thinner consistency than the cream emulsion form.

A more complete listing and description of components useable in the cosmetic compositions, ranges, ratios, and particular embodiments are provided below.

Cholesterol

The cosmetic compositions of the present disclosure include cholesterol, often as the most dominant lipid in the composition. The amount of cholesterol in the compositions may be at least 1.0 wt. %, 1.5 wt. %, 2.0 wt. %, 2.5 wt. %, 3.0 wt. %, 3.5 wt. % or 4 wt. %, and as high as 5.0 wt. %, 6.0 wt. %, 7.0 wt. %, 8.0 wt. %, 9.0 wt. %, 10 wt. %, or 15 wt. %. The total amount of cholesterol in the cosmetic composition may be greater than the total amount of the one or more ceramides in the composition. The ratio of the total amount of cholesterol to the total amount of the one or more ceramides may be from 1.1:1.0, 1.5:1.0, 1.8:1, 2.0:1.0, 2.5:1.0, 3.0:1.0, 3.5:1, or 4.0:1.0 to 4.5:1.0, 5.0:1.0, 6.0:1.0, 7.0:1.0, 8.0:1.0, 9.0:1.0 or 10:1.0.

Ceramides

Ceramides are a family of waxy lipid molecules that are composed of sphingosine and a fatty acid. Ceramides include ceramide 1, ceramide 2, ceramide 3, ceramide 4, ceramide 5, ceramide 1A, ceramide 6 II, ceramide AP, ceramide EOP, ceramide EOS, ceramide NP, ceramide NG, ceramide NS, ceramide AS, and ceramide NS dilaurate. In some instances, the cosmetic compositions of the instant disclosure include ceramide 3, optionally in combination with one or more other ceramides. In other instances, the cosmetic compositions include ceramide EOP, optionally in combination with one or more other ceramides. The cosmetic compositions may include two, three, or more ceramides. For example, ceramide 3 and ceramide EOP (or any other combination of two or more ceramides) could be included in the cosmetic compositions.

The total amount of the one or more ceramides in the cosmetic compositions may be at least 0.1 wt. %, 0.2 wt. %, 0.3 wt. %, 0.4 wt. %, 0.5, wt. %, 0.6 wt. %, 0.7 wt. %, 0.8 wt. %, 0.9 wt. %, 1.0 wt. %, 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, or 2.0 wt. % to 2.5 wt. %, 3.0 wt. %, 3.5 wt. %, 4.0 wt. %, or 5 wt. %.

In some instances, the total amount of cholesterol and the one or more ceramides in the cosmetic compositions are at least 1 wt. %, 2 wt. %, 3 wt. %, 4 wt. %, 5 wt. %, or 6 wt.

%, and may be in an amount up to 7 wt. %, 8 wt. %, 9 wt. %, 10, wt. %, 11 wt. %, 12 wt. %, 13 wt. %, 14 wt. %, 15 wt. %, or higher.

Oils

The cosmetic composition comprises one or more oils, for example, silicone oils, fluoro oils, hydrocarbon-based oils, etc. The term "oil" means any fatty substance which is in liquid form at room temperature (20-25° C.) and at atmospheric pressure (760 mmHg). Often, at least one of the oils in the cosmetic composition is part of an oily phase. An "oily phase" is a phase comprising at least one oil that may include additional liposoluble and lipophilic ingredients and the fatty substances. Oil that is suitable for use herein may be volatile or non-volatile. The term "volatile oil" relates to an oil that is capable of evaporating on contact with the skin or a keratin fiber in less than one hour, at room temperature and atmospheric pressure. The volatile oil(s) are liquid at room temperature and have a non-zero vapor pressure, at room temperature and atmospheric pressure, ranging in particular from 0.13 Pa to 40 000 Pa ($10^{-3}$ to 300 mmHg). The term "non-volatile oil" relates to oil which remains on the skin or the keratin fiber, at room temperature and atmospheric pressure, for at least several hours and which in particular has a vapor pressure of less than $10^{-3}$ mmHg (0.13 Pa).

The term "silicone oil" relates to oil comprising at least one silicon atom, and especially at least one Si—O group. The term "fluoro oil" relates to oil comprising at least one fluorine atom. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil or a synthetic hydrocarbon-based oil. Further, suitable oil may be a mineral hydrocarbon-based oil, a plant hydrocarbon-based oil, or a synthetic hydrocarbon-based oil.

The amount of the one or more oils in the composition may vary, and may be from 20 wt. % to 80 wt. %, 30 wt. % to 70 wt. %, or from 40 wt. % to 60 wt. %. Further, the amount of the one or more oils may be 20, 25, 30, 35, or 40 wt. % to 50, 55, 60, 65, 75, or 80 wt. %.

Silicone Oils

The cosmetic compositions described herein may comprise one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl) trimethylsiloxysilicates.

Other examples of silicone oils that may be mentioned include volatile linear or cyclic silicone oils, especially those with a viscosity 8 centistokes ($8 \times 10^6$ m²/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Fluoro Oils

The cosmetic compositions described herein may comprise one or more fluoro oils. For example, the one or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The cosmetic compositions described herein may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the compositions include a synthetic oil selected from the group consisting of hydrogenated polyisobutene and hydrogenated polydecene.

The hydrocarbon-based oil may be a non-volatile hydrocarbon-based, such as:

(i) hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and 4 0 squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is ≥10, for instance Purcellin oil (cetearyl octanoate), isopropyl myristate, isopropyl palmitate, $C_{12}$-$C_{15}$ alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by Enichem Augusta Industriale, and also di(linear $C_{14}$-$C_{15}$ alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC® by Cognis;

(viii) fatty amides, such as isopropyl N-lauroyl sarcosinate, such as the product sold under the trade name Eldew SL 205® from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

In certain instances, the non-volatile hydrocarbon-based oils are glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, such as octyldodecanol.

As volatile hydrocarbon-based oils, mention is made of hydrocarbon-based oils containing from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane or isohexadecane, the oils sold under the Isopar or Permethyl trade names, branched C $C_8$-$C_{16}$ esters, and isohexyl neopentanoate.

As mentioned previously, one or more oils of the cosmetic composition is often part of an oily phase. The oily phase may include other fatty substances, mixed with or dissolved in the oil. A fatty substance that may be present in the oily phase may be, for example:

(i) a fatty acid chosen from fatty acids comprising from 8 to 30 carbon atoms, such as stearic acid, lauric acid, palmitic acid and oleic acid;

(ii) a wax chosen from waxes such as lanolin, beeswax, carnauba or candelilla wax, paraffin waxes, lignite waxes, microcrystalline waxes, ceresin or ozokerite, or synthetic waxes, such as polyethylene waxes or Fischer-Tropsch waxes;

(iii) a gum;

(iv) a pasty compound, such as polymeric or non-polymeric silicone compounds, esters of a glycerol oligomer, arachidyl propionate, fatty acid triglycerides and derivatives thereof.

The overall oily phase may represent 5 wt. % to 95 wt. %, 10 wt. % to 80 wt. %, 20 wt. % to 70 wt. %, or 30 wt. % to 60 wt. % of the cosmetic composition. The overall aqueous phase may represent 5 wt. % to 95 wt. %, 20 wt. % to 90 wt. %, 30 wt. % to 80 wt. %, or 40 wt. % to 70 wt. % of the cosmetic composition.

Emulsifiers

The cosmetic compositions described herein may include one or more emulsifiers. For example the emulsifier may be an amphoteric, anionic, cationic or nonionic emulsifier, used alone or as a mixture, and optionally with a co-emulsifier. The emulsifiers are chosen in an appropriate manner according to the emulsion to be obtained. The total amount of emulsifiers in the composition are typically in an amount of 0.1 wt. % to 30 wt. %, 0.1 wt. % to 20 wt. %, 0.5 wt. % to 20 wt. %, 1 wt. % to 20 wt. %, 1 wt. % to 15 wt. %, or 1 wt. % to 10 wt. %, or from 0.5, 0.6, 0.7, 0.8, 0.9 or 1.0 wt. % to 5, 6, 7, 8, 9, or 10 wt. %.

For W/O emulsions, examples of emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM 90™ by the company Goldschmidt.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

In some instance, the one or more emulsifiers include an oganosiloxane emulsifier, including crosslinked organosiloxane emulsifiers. For example, the compositions may comprise one or more crosslinked organosiloxane emulsifier selected from the group consisting of dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer.

In another embodiment, the compositions include one or more linear organosiloxane emulsifier selected from the group consisting of cyclotetrasiloxane (and) cyclopentasiloxane (and) PEG/PPG-18 dimethicone, cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone.

Usable oxyalkylenated organosiloxane emulsifier include the following:

An oxyalkylenated organosiloxane emulsifier having the general formula:

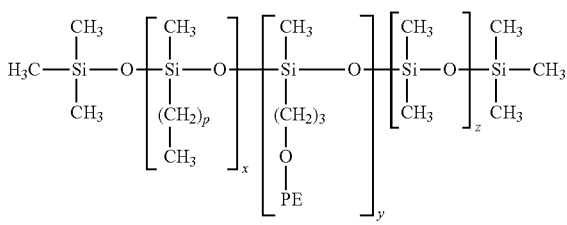

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0-25, b is 0-25 with the proviso that both a and b cannot be 0 simultaneously, x, y, and z are each independently ranging from 0 to 1 million with the proviso that x and y cannot be 0 simultaneously. In some cases, x, y, z, a, and b are such that the molecular weight of the polymer ranges from about 5,000 to about 500,000, from about 10,000 to 100,000, or is about 50,000, and the polymer is generically referred to as dimethicone copolyol. In some instances, p is such that the long chain alkyl is cetyl or lauryl, and the compound is called, generically, cetyl dimethicone copolyol or lauryl dimethicone copolyol respectively. In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or ether, such as methyl ether, ethyl ether, propyl ether, butyl ether, and the like.

An oxyalkylenated organosiloxane emulsifier having the general formula:

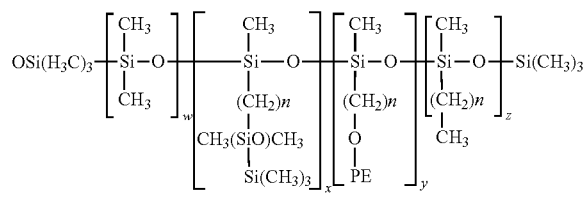

wherein each n is independently 0-100 with the proviso that there must be at least one PE radical. In some instances, where each n independently ranges from about 2 to 30, and PE $(-C_2H_4O)_a-(-C_3H_6O)_b-H$ wherein a is 0-25, b is 0-25 with the proviso that both a and b cannot simultaneously be 0; and wherein w, x, y, and z are each independently 0 to 1,000,000 with the proviso that there is at least one PE. In some embodiments the organosiloxane emulsifier is lauryl PEG-9 Polydimethylsiloxyethyl Dimethicone. Oxyalkylenated organosiloxane emulsifiers disclosed in U.S. Pat. No. 9,095,543 are useful in the instant compositions. U.S. Pat. No. 9,095,543 is incorporated herein by reference in its entirety.

Further examples of organosiloxane emulsifiers include those having C.T.F.A. names Bis-Butyldimethicone Polyglyceryl-3; Bis-PEG/PPG-14/14 Dimethicone; Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-15 Acetate; Dimethicone PEG-7 Cocoate; Dimethicone PEG-7 Phosphate; Dimethicone PEG-10 Phosphate; Dimethicone PEG/PPG-7/4 Phosphate; Dimethicone PEG/PPG-12/4 Phosphate; Dimethicone PEG-7 Undecylenate; Lauryl Dimethicone PEG-10 Phosphate; Isopolyglyceryl-3 Dimethicone; Isopolyglyceryl-3 Dimethiconol; Isostearyl Carboxyldecyl PEG-8 Dimethicone; Lauryl Methicone PEG-10 Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG-20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydimethylsiloxyethyl Dimethicone; PPG-12 Butyl Ether Dimethicone; Silicone Quaternium-17; TEA-Dimethicone PEG-7 Phosphate; or mixtures thereof.

Further examples of commercial linear organosiloxane emulsifiers are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of fully or partially cross-linked oxyalkylenated organosiloxane emulsifiers. They may be elastomeric or non-elastomeric. They are sometimes referred to as "emulsifying elastomers" because of they have both elastomeric and emulsifying properties.

Polyoxyalkylenated silicone elastomers that may be used in at least one embodiment include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers include dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

Further examples of crosslinked organosiloxane emulsifiers include, but are not limited to Dimethicone/dimethicone PEG/PPG 15 crosspolymer; Dimethicone PEG-10 crosspolymer; Dimethicone PEG-10/15 Crosspolymer; Dimethicone PEG-15 Crosspolymer; Dimethicone Polyglycerin-3 Crosspolymer; Dimethicone PPG-20 Crosspolymer; Dimethiconol/Methylsilanol/Silicate Crosspolymer; Dimethiconol/Silicate Crosspolymer; Lauryl Dimethicone PEG-15 Crosspolymer; Lauryl Dimethicone Polyglycerin-3 Crosspolymer; PEG-8 Dimethicone Polysorbate-20 Crosspolymer; PEG-10 Dimethicone/Vinyl Dimethicone Crosspolymer; PEG-10 Lauryl Dimethicone Crosspolymer; PEG-15/Lauryl Dimethicone Crosspolymer; and PEG-15 Laurylpolydimethylsiloxyethyl Crosspolymer.

Thickeners

The cosmetic compositions described herein may include one or more thickeners. The thickeners may be in an amount of 0.1 wt. % to 20 wt. %, 0.1 to 10 wt. %, 0.1 wt. % to 9 wt. %, 0.2 wt. % to 9 wt. %, 0.3 wt. % to 9 wt. %, 0.4 wt. % to 8 wt. %, 0.5 wt. % to 5 wt. %, 1 wt. % to 5 wt. %, or 2 wt. % to 4 wt. %. Further, the amount of thickener may be from 0.1, 0.2, 0.3, 0.4, 0.5, 0.6, 0.7, 0.8, 0.9, 1.0, or 1.5 wt. % to 2, 3, 4, 5, 6, 7, 8, 9, 10, 15, or 20 wt. %.

The one or more thickeners may be xanthan gum, guar gum, biosaccharide gum, cellulose, acacia Seneca gum, sclerotium gum, agarose, pechtin, gellan gum, hyaluronic acid. Additionally, the one or more thickeners may include polymeric thickeners selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some cases, the composition includes ammonium polyacryloyldimethyl taurate and/or sodium polyacrylate.

Many thickeners are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water. Non-limiting examples of various types of thickeners include:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the cross-linking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

b. Crosslinked Polyacrylate Polymers

The compositions of the present disclosure can optionally contain crosslinked polyacrylate polymers useful as thickeners or gelling agents including both cationic and nonionic polymers. Examples of useful crosslinked nonionic polyacrylate polymers and crosslinked cationic polyacrylate polymers are those described in U.S. Pat. No. 5,100,660, U.S. Pat. No. 4,849,484, U.S. Pat. No. 4,835,206, U.S. Pat. No. 4,628,078 U.S. Pat. No. 4,599,379 and EP 228,868, which are all incorporated herein by reference in their entirety.

c. Polyacrylamide Polymers

The compositions of the present disclosure can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

d. Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™. CS11 from Michel Mercier Products Inc.

e. Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived form callus of plants belonging to *Polyantes* sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Active Ingredients

The cosmetic compositions described herein may include one or more active ingredients. The compositions may include 10 ppm to 10 wt. % (100,000 ppm), 10 ppm to 5 wt. % (50,000 ppm), 10 ppm to 2.5 wt. % (25,000 ppm), 10 ppm to 1 wt. % (10,000 ppm), 10 ppm to 0.5 wt. % (5,000 ppm), 10 ppm to 0.1 wt. % (1,000 ppm), or 10 ppm to 500 ppm of one or more active ingredients. In some cases, the one or more active ingredients is present in an amount from 10, 20, 30, 40, 50, 60, 70, 80, 90, 100, 150, or 200 ppm to 500, 600, 700, 800, 900, 0.1 wt. % (1000 ppm), 0.5 wt. % (5,000 ppm), 1 wt. % (10,000 ppm)), 5 wt. % (50,000 ppm), or 10 wt. % (100,000 ppm).

Non-limiting examples of the one or more active agents include adenosine, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, and a coenzyme. In some cases the active ingredient is adenosine.

In one embodiment the formulation comprises an active ingredient such as a humectant and moisturizing ingredients, an anti-aging agent, a depigmenting agent, an anti-wrinkle agent, or an agent that treats oily skin.

Humectants and moisturizing ingredients may be in particular glycerol and its derivatives, urea and its derivatives, especially Hydrovance marketed by National Starch, lactic acid, hyaluronic acid, AHA, BHA, sodium pidolate, xylitol, serine, sodium lactate, ectoin and its derivatives, chitosan and its derivatives, collagen, plankton, an extract of *Imperata cylindra* sold under the name Moist 24 by Sederma, homopolymers of acrylic acid as Lipidure-HM of NOF Corporation, beta-glucan and in particular sodium carboxymethyl beta-glucan Mibelle-AG-Biochemistry, a mixture of oils passionflower, apricot, corn, and rice bran sold by Nestle under the name NutraLipids, a C-glycoside derivatives, in particular the C-13-D-xylopyranoside-2-hydroxypropane in the form of a solution at 30% by weight of active material in a water/propylene glycol mixture (60/40 wt %) as the product produced by the company Chimex under the trade name "Mexoryl SBB", a rose hip oil marketed by Nestle, a micro-algae extract Prophyridium cruentum enriched with zinc, marketed under the name by Vincience Algualane Zinc spheres of collagen and chondroitin sulfate of marine origin (Atelocollagen) sold by the company Engelhard Lyon under the name Marine Filling Spheres, hyaluronic acid spheres such as those marketed by Engelhard Lyon, and arginine.

Depigmenting agents include vitamin C and its derivatives and especially vitamin CG, CP and 3-O ethyl vitamin C, alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, ceramides and their counterparts, derived from plants such as chamomile, bearberry, the aloe family (vera, ferox, bardensis), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include vitamin C and its derivatives and especially vitamin CG, CP and 3-O ethyl vitamin C, alpha and beta arbutin, ferulic acid, kojic acid, resorcinol and derivatives, D pantheteine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

The term "anti-wrinkle active" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Exemplary anti-wrinkle actives may be chosen from: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof.

Examples of such compounds are: adenosine and its derivatives and retinol and its derivatives such as retinol palmitate, ascorbic acid and its derivatives such as magnesium ascorbyl phosphate and ascorbyl glucoside; tocopherol and derivatives thereof such as tocopheryl acetate, nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxypropane as described in particular in EP-1345919, plant extracts including sea fennel and extracts of olive leaves, as well as plant and hydrolysates thereof such as rice protein hydrolysates or soybean proteins; algal extracts and in particular *laminaria*, bacterial extracts, the sapogenins such as diosgenin and extracts of *Dioscorea* plants, in particular wild yam, comprising: the a-hydroxy acids, f3-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof.

As adenosine derivatives include especially non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside.

Other derivatives include adenosine receptor agonists such as adenosine adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxy-ethyl) phenethyl-amino-5'-N-ethylcarboxamido adenosine (CGS-21680), N-ethylcarboxamido-adenosine (NECA), the 5'(N-cyclopropyl)-carboxamidoadenosine, DPMA (PD 129.944) and metrifudil.

In one embodiment the composition comprises an active ingredient that addresses oily skin. These actives can be sebo-regulating or antiseborrhoeic agents capable of regulating the activity of sebaceous glands. These include: retinoic acid, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol A5—zinc salts such as zinc gluconate, zinc pyrrolidonecarboxylate (or zinc pidolate), zinc lactate, zinc aspartate, zinc carboxylate, zinc salicylate 20, zinc cysteate;—derivatives particularly copper and copper pidolate as Cuivridone Solabia—extracts from plants of *Arnica montana, Cinchona succirubra, Eugenia caryophyllata, Humulus lupulus, Hypericum perforatum, Mentha pipenta* 25 *Rosmarinus officinalis, Salvia officinalis* and *Thymus vulgaris*, all marketed for example by Maruzen—extracts of meadowsweet (*Spiraea ulmaria*), such as that sold under the name Sebonormine by Silab—extracts of the alga *Laminaria saccharina*, such as that sold under the 30 name Phlorogine by Biotechmarine—the root extracts of burnet mixtures (*Sanguisorba officinalis/Poterium officinale*), rhizomes of ginger (*Zingiber officinalis*) and cinnamon bark (*Cinnamomum cassia*), such as that sold under the name Sebustop by Solabia—extracts of flaxseed such as that sold under the name Linumine by Lucas Meyer—Phellodendron extracts such as those sold under the name Phellodendron extract BG by Maruzen or Oubaku liquid B by Ichimaru Pharcos—of argan oil mixtures extract of *Serenoa serrulata* (saw palmetto) extract and sesame seeds such as that sold under the name Regu SEB by Pentapharm—mixtures of extracts of willowherb, of Terminalia chebula, nasturtium and of bioavailable zinc (microalgae), such as that sold under the name Seborilys Green Tech;—extracts of *Pygeum afrianum* such as that sold under the name *Pygeum afrianum* sterolic lipid extract by Euromed—extracts of *Serenoa serrulata* such as those sold under the name *Viapure Sabal* by Actives International, and those sold by the company Euromed—of extracts of plantain blends, *Berberis aquifolium* and sodium salicylate 20 such as that sold under the name Seboclear Rahn—extract of clove as that sold under the name Clove extract powder by Maruzen—argan oil such as that sold under the name Lipofructyl Laboratories Serobiologiques; 25—lactic protein filtrates, such as that sold under the name Normaseb by Sederma—the seaweed *laminaria* extracts, such as that sold under the name Laminarghane by Biotechmarine—oligosaccharides seaweed *Laminaria digitata*, such as that sold under the name Phycosaccharide 30 AC by the company Codif—extracts of sugar cane such as that sold under the name Policosanol by the company Sabinsa, the sulfonated shale oil, such as that sold under the name Ichtyol Pale by Ichthyol—extracts of meadowsweet (*Spiraea ulmaria*) such as that sold under the name Cytobiol Ulmaire by societeLibiol—sebacic acid, especially sold in the form of a sodium polyacrylate gel under the name Sebosoft by Sederma—glucomannans extracted from konjac tuber and modified with alkylsulfonate chains such as that sold under the name Biopol Beta by Arch Chemical—extracts of *Sophora angustifolia*, such as those sold under the name *Sophora* powder or *Sophora* extract by Bioland—extracts of *cinchona* bark succirubra such as that sold under the name Red Bark HS by Alban Muller—extracts of *Quillaja saponaria* such as that sold under the name 15 Panama wood HS by Alban Muller—glycine grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20—phthalimidoperoxyhexanoic acid—citrate tri (C12-C13) sold under the name COSMACOL® ECI by Sasol; trialkyl citrate (C14-C15) sold under the name COSMACOL® ECL by Sasol—10-hydroxydecanoic acid, including mixtures acid-hydroxydecanoic October 25, sebacic acid and 1,10-decandiol such as that sold under the name Acnacidol BG by Vincience and mixtures thereof.

The instant disclosure also relates to methods or processes for making/manufacturing the cosmetic compositions described herein. It also encompasses the products prepared by these methods or processes. Typically, a process for making the cosmetic compositions of the instant disclosure comprises the formation of a fatty phase and the formation of a separate aqueous phase (containing water), both phases are heated and combined while warm. Each phase may be heated to the same temperature or may be heated to different temperatures. Typically the phases are individually heated to a temperature of at least 60, 65, 70, 75, 80, or 90° C. to 110° C. For example, one or more of the phases may be heated to a temperature of about 60-110° C., 70-100° C., 80-100° C., 85-100° C., or 85-95° C.

In some embodiments, the cholesterol, one or more ceramides, and one or more oils are combined in the fatty phase. Additionally, in some cases, one or more emulsifiers and one or more thickeners are also combined in the fatty phase. Water soluble thickeners may be added to the aqueous phase of the cosmetic compositions. However, in some cases water soluble thickeners (e.g., sodium polyacrylate, etc.) can be advantageously added to the fatty phase instead of the water phase before emulsification to help stabilize and incorporate high amounts of cholesterol and one or more ceramides into the compositions. In some cases, water soluble thickeners may also be added post-emulsification. For examples, in some instances, ammonium polyacryloyldimethyl taurate, may be added post-emulsification.

After combining the fatty phase and the aqueous phase to form an emulsion, the composition is typically allowed to cool. Additional components may be added during the time of emulsification or after. For example, certain fragrances, colorings, exfoliants, active ingredients, etc., maybe added to the aqueous phase, the fatty phase, or after emulsification.

The instant disclosure also relates to methods of using the cosmetic compositions described herein. For example, the cosmetic compositions can be used in a method for supporting natural lipid barrier function of skin, wherein the method comprises applying the composition to skin or hair. Typically, the cosmetic compositions are applied to this skin or hair of humans. In some cases, the composition is applied to the face. Furthermore, the cosmetic composition can be used in methods for treating dryness of the skin and/or hair, repairing damage to skin and/or hair (for example, damage from photoaging), and for diminishing the appearance of wrinkles, dark spots, and uneven skin texture of skin. These methods also entail application of the cosmetic compositions described herein to the skin and/or hair, and in some cases to the face. The cosmetic composition may be applied once per day, twice per day, or more than once or twice per day. In some cases, the composition is applied in the evenings before bed. In other cases, the compositions are applies in the morning. In still other cases, the composition may be applied immediately after washing the skin and/or hair. The compositions may be used once, or for a series of days, weeks, or months. For example, the compositions may be used daily for a period of 1, 2, 3, 4, 5, 6, 7, 8 or more weeks, or months.

Implementation of the present disclosure is provided by way of the following examples. The examples serve to illustrate the technology without being limiting in nature.

Example 1

Restorative Cream

A restorative cream was prepared as a water-in-oil emulsion. Instead of ceramides as the dominant lipid component, the restorative cream contains cholesterol as the dominant lipid component. The components of the cream are presented in Table 1, below.

TABLE 1

| Phase | INCI Name | Concentration |
|---|---|---|
| A1 | WATER | 45-65 |
| A1 | GLYCERIN | 1-10 |
| A1 | HYDROXYETHYLPIPERAZINE ETHANE SULFONIC ACID | 0.1-1 |
| A1 | PROPYLENE CARBONATE | 0.01-2 |
| A1 | PHENOXYETHANOL | 0.01-2 |
| A1 | CHLORPHENESIN | 0.01-2 |
| A1 | DISODIUM EDTA | 0.01-4 |
| A1 | CAPRYLYL GLYCOL | 0.01-4 |
| A1 | ADENOSINE | 0.01-0.1 |
| A2 | AMMONIUM POLYACRYLOYLDIMETHYL TAURATE | 0.01-3 |
| A2 | SODIUM POLYACRYLATE | 0.1-3 |
| B1 | HYDROGENATED POLYISOBUTENE | 1-20 |
| B1 | DIMETHICONE (and) DIMETHICONE/PEG-10/15 CROSSPOLYMER | 1-10 |
| B1 | PEG-10 DIMETHICONE | 0.1-5 |
| B1 | C12-15 ALKYL BENZOATE | 0.1-5 |

TABLE 1-continued

| Phase | INCI Name | Concentration |
|---|---|---|
| B1 | CERAMIDE 3 | 0.1-5 |
| B1 | CHOLESTEROL | 1-10 |
| B1 | LAURYL PEG-9 POLYDIMETHYLSILOXYETHYL DIMETHICONE | 0.1-5 |
| B1 | BIS-PEG-18 METHYL ETHER DIMETHYL SILANE | 0.1-5 |
| B1 | CERAMIDE EOP | 0.001-5 |
| B1 | *HELIANTHUS ANNUUS* (SUNFLOWER) SEED OIL UNSAPONIFIABLES | 0.1-5 |
| B2 | DISTEARDIMONIUM HECTORITE | 0.1-3 |
| C | DIMETHICONE | 5-15 |
| D | NYLON-12 | 0.01-5 |
| D | ACRYLONITRILE/METHYL METHACRYLATE/VINYLIDENE CHLORIDE COPOLYMER | 0.01-5 |
| D | DIMETHICONE (and) PEG/PPG-18/18 DIMETHICONE | 0.01-2 |
| E | FRAGRANCE (Essential Oils) | 0.01-0.5 |
| | TOTAL | 100 |

In order to incorporate the high levels of ceramide-3 and cholesterol, the oil phase and water phase were heated to 85-95° C. This helps prevent recrystallization of the ceramide-3 and ceramide-EOP. The thickener, sodium polyacrylate was added to the oil phase rather than to the water phase or during post emulsification. Both phases were maintained at 85-95° C. during emulsification. The second thickener, ammonium polyacryloyldimethyl taurate, was added post emulsification. To stabilize ceramide-EOP and the high levels of ceramide-3 and cholesterol in the formula, the following combination of W/O emulsifiers was used: PEG-10 Dimethicone, Dimethicone (and) Dimethicone/PEG 10/15 Crosspolymer, Lauryl PEG-9 Polydimethylsiloxyethyl Dimethicone, and Dimethicone (and) PEG/PPG-18/18 Dimethicone.

Example 2

Improving Skin Hydration and Repairing Skin Barrier Function

A clinical study was carried out to evaluate the restorative cream of Example 1. The study investigated the effectiveness of the restorative cream in improving skin hydration and repairing skin barrier function. A total of twenty-seven (27) female subjects, ranging in age from 55-73 years, consented, enrolled, and completed the study.

Changes in skin conductance, impedance or capacitance are used to study epidermal hydration in vivo. The measurement is made on the difference in dielectric constant; skin has a low dielectric constant and water has a high dielectric constant of 81. When skin is hydrated, conductance and capacitance increases and impedance decreases. The measuring capacitor shows changes in capacitance according to the moisture content of the tissue.

Corneometer CM 825 (Courage and Khazaka, Germany) was used to measure the electrical capacitance/hydration of the skin. Three replicate measurements were taken from randomized treatment sites for the restorative cream and the control site (untreated skin) at each measurement interval. If one measurement was more than ±10 units from the other measurements this measurement was not included in the analysis. Transpeidermal water loss (TWEL) is a measure of skin barrier function. The evaporimeter probe has two sensors, which measure the vapor pressure gradient arising within the device's chamber and between the skin and the surrounding air. TEWL was measured using DermaLab Evaporimeter (Cortex Technology, Hadsun, Denmark). Decreases in TEWL indicates a repair in skin barrier function, such that less water is lost through the skin barrier. TEWL measurements were taken from the randomized designated treatment sites for the restorative cream and the control sites (untreated skin) at each measurement interval.

Three days prior to the start of the study, enrolled subjects began the washout period. Subject received a neutral soap bar (Neutrogena) to use for cleansing their volar forearms (i.e., bathing) for the washout period. Subject were given specific instructions prohibiting the use of all personal care products (e.g., lotions, creams), on the test site (volar forearms) for the entire washout and study duration.

Following the washout period, subject returned to the testing facility for baseline measurements. The volar surface At 1 hour post-treatment skin hydration readings were again taken. Also at 1 hour post-treatment TEWL readings were taken at sites C and D by Evaporimeter. At 2 and 4 hours post-treatment, the TEWL readings were again taken. At 8 hours post-treatment both skin hydration readings (for sites A and B) and TEWL readings (for sites C and D) were taken. Subjects were dismissed after the 8 hour post-treatment measurements were obtained but were instructed not to wet (e.g., no shower, bathing, or swimming) or apply products to their volar forearms until after the 24 hour measurements were obtained. Approximately 24 hours (±30 min) after product application to the test sites, subjects returned for measurements for the final skin hydration measurements. An outline of the testing timeline is presented in Table 2, below, along with the results of the tests.

TABLE 2

| Procedure | Visit 1 3-days prior | Visit 2 Baseline | Tape | 0 h (15 min) | 1 h | 2 h | 4 h | 8 h | Visit 3 24 h |
|---|---|---|---|---|---|---|---|---|---|
| Distribute Washout product | X | | | | | | | | |
| Corneometer Measurements (Sites A and B) | | X | | X | X | | | X | X |
| TEWL Measurements (Sites C and D) | | X | X | | X | X | X | X | |
| Tape-Strip sites to TEWL value greater than 20 g/m2/h (sites C and D) | | X | X | | | | | | |
| Product Application (sites A and C) | | | | X | | | | | |
| Results | | | | | | | | | |
| Improvement in skin hydration | | | ✓ | ✓ | — | — | ✓ | | ✓ |
| Improvement in skin barrier function (TEWL) | | | — | ✓ | ✓ | ✓ | ✓ | | — |

"✓" indicates a statistically significant improvement when compared to untreated site ($p \leq 0.05$).
"—" indicates that no measurement was taken at this time interval.

of the forearms were gently wiped with a damp disposable washcloth and patted dry with a paper towel. Four test sites were marked on the volar surfaces of the forearms (two sites on each forearm). Each test site was 4 cm by 4 cm. Test sites were placed at least 2 cm from the wrist joint and at least 2 cm from elbow joint and were identified as Test Sites A-D. The treatment sites and control sites (untreated) were randomly assigned using a computer generated randomization code.

To determine baseline (pre-treatment), skin hydration readings were taken by Corneometer for sites A and B. TEWL readings by Evaporimeter were taken for sites C and D. Packing tape was applied to the designated sites (Site C) and control (untreated) (Site D) TWEL sites. The tape was then stripped from the sites. TEWL readings by Evaporimeter were performed and repeated taping and stripping carried out until a TWEL measurement greater than 20 g/m² h was reached.

Following baseline measurements (post tape stripping), application of the restorative cream on the designated treatment test sites was performed. Approximately 2 mg/cm² of the restorative cream was applied to the designated treatment sites (A and C). After application, subjects remained in the exam room and were instructed to keep their volar forearms uncovered and exposed. After 15 minutes post-treatment (±5 min), skin hydration readings were taken by Corneometer for sites A and B.

At baseline there was no statistical significant difference in skin hydration measurement between the untreated and treated sites. When evaluating hydration over time for sites treated with restorative cream, there was a statistical significant increase (improvement) in skin hydration measurements when compared to baseline measurements. When evaluating hydration over time for untreated sites, however, there was no statistical significant difference in skin hydration measurement when compared to baseline measurement at 15 minutes, 1 hour, and 8 hours. At 24 hours, there was a statistical significant decrease (worsening) in skin hydration measurement when compared to baseline.

Example 3

Improving Skin Hydration and Protecting Skin Barrier Function

A clinical study was carried out to evaluate the effectiveness of the restorative cream of Example 1 in protecting skin barrier function. A total of twenty-six (26) female subjects, ranging in age from 55-71 years, consented, enrolled, and completed the study. Three days prior to the start of the study, enrolled subjects began the washout period. Subject received a neutral soap bar (Neutrogena) to use for cleansing their volar forearms (i.e., bathing) for the washout period. Subject were given specific instructions prohibiting the use of all personal care products (e.g., lotions, creams), on the test site (volar forearms) for the entire washout and study duration.

Following the washout period, subject returned to the testing facility for baseline measurements. The volar surface of the forearms were gently wiped with a damp disposable washcloth and patted dry with a paper towel. Two test sites were marked on the volar surfaces of the forearms (one site on each forearm). Each test site was 4 cm by 4 cm. Test sites were placed at least 2 cm from the wrist joint and at least 2 cm from elbow joint and were identified as Test Sites A and B. The treatment sites and control sites (untreated) were randomly assigned using a computer generated randomization code.

To determine baseline (pre-treatment), TEWL readings by Evaporimeter were taken at sites A and B. Subjects were given the restorative cream to use twice a day on one volar forearm (per computer generated randomization) for one week.

After one week, subjects returned to the testing facility. The volar surface of the forearms were gently wiped with a damp disposable washcloth and patted dry with a paper towel. Then, TEWL readings by Evaporimeter were taken at sites A and B.

Following the one week post-treatment TEWL readings a, packaging tape (Office Depot brand) was then applied to the treated site and the control (untreated) site. Following twelve consecutive tape stripping of each site, TEWL readings by Evaporimeter were again taken. An outline of the testing timeline is presented in Table 3, below, along with the results of the tests.

TABLE 3

| Procedure | Visit 1 3-days prior | Base- line | Visit 2 Pre-Tape Strip (one week) | Post-Tape Strip (one week) |
|---|---|---|---|---|
| Distribute Washout product | X | | | |
| Restorative Cream Distribution | | X | | |
| TEWL Measurements (Sites A and B) | | | X | X |
| Results | | | | |
| Improvement in Skin Hydration | | | | ✓ |
| Protects Skin Barrier Function | | | ✓ | |

"✓" indicates a statistically significant improvement ($p \leq 0.05$).

There was a statistical difference when comparing the baseline TEWL values for the untreated and treated sites. Skin treated with the restorative cream significantly decreased TEWL values after one week of product use when compared to baseline and to the untreated control site, indicating an improvement in skin barrier function after one week.

There was also a statistical difference when comparing the pre-tape strip TEWL values for the untreated and treated sites. Furthermore, TEWL values were significantly higher after tape stripping on both the treated and the untreated sites, when compared to before tape stripping. When comparing between the treated and the untreated sites, the treated sites showed a significantly smaller increase in TEWL values, indicating that the restorative cream provides a protective effect after one week of use.

Example 4

Evaluation of Efficacy and Tolerance

A clinical study was carried out to evaluate the efficacy and tolerance of the restorative cream of Example 1. A total of fifty-five (55) individuals used the restorative cream for 8 weeks. Individuals used the restorative cream for 8 weeks and various effects were evaluated immediately upon application at the start of the trial, after four weeks of use, and after eight weeks of use. The results are presented in Table 4, below.

TABLE 4

| Assessment | Method | Immediate | Week 4 | Week 8 |
|---|---|---|---|---|
| Improvement in skin dryness | Clinical | | | |
| Improvement in skin tone evenness | Clinical | | ✓ | ✓ |
| Improvement in skin brightness/radiance/luminosity | Clinical | Not Evaluated | ✓ | ✓ |
| | | ✓ | ✓ | ✓ |
| Improvement in fine lines/wrinkles | Clinical | Not Evaluated | ✓ | ✓ |
| Improvement in skin tone clarity | Clinical | Not Evaluated | ✓ | ✓ |
| Improvement in skin firmness | Clinical | Not Evaluated | ✓ | ✓ |
| Improvement in skin laxity/elasticity | Clinical | Not Evaluated | ✓ | ✓ |
| Improvement in pore appearance | Clinical | ✓ | ✓ | ✓ |
| Improvement in overall appearance of skin's condition | Clinical | | ✓ | ✓ |
| Transepidermal Water Loss | Instrumental | | | ✓ |
| Corneometer | Instrumental | | ✓ | ✓ |

"✓" indicates a statistically significant improvement.

There was a statistically significant decrease (improvement) immediately after the first product application for skin texture/smoothness and pore appearance when compared to baseline. There was also a statistically significant decrease (improvement) in skin tone evenness, skin brightness/radiance/luminosity, skin texture/smoothness, fine lines/wrinkles, skin tone clarity, skin firmness, skin laxity/elasticity, pore appearance and overall appearance at week 4 and at week 8 when compared to baseline. There was a statistically significant improvement in TWEL at week 8 when compared to baseline, and a statistically significant increase (improvement) in skin hydration at both week 4 and week 8 when compared to baseline.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "at least one" means one or more and thus includes individual components as well as mixtures/combinations.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A ready to use cosmetic composition in the form of an emulsion comprising:
    (a) 2 wt. % to 8 wt. % of cholesterol, based on the total weight of the cosmetic composition;
    (b) 1 wt. % to 5 wt. % of non-crystallized ceramide-3 and non-crystallized ceramide-EOP, based on the total weight of the cosmetic composition,
    wherein the ratio of (a) to (b) is 1.5:1.0 to 5:1.0;
    (c) one or more silicone oils and one or more hydrocarbon based oils;
    (d) 0.5 wt. % to 10 wt. % of one or more organosiloxane emulsifiers;
    (e) 0.1 wt. % to 10 wt. % of one or more thickeners; and
    (f) 45 wt. % to 65 wt. % of water, based on the total weight of the cosmetic composition.

2. The cosmetic composition of claim 1 comprising one or more silicone oils selected from the group consisting of dimethicone, cyclomethicone, polysilicone-11, phenyl trimethicone, trimethylsilylamodimethicone, and stearoxytrimethylsilane.

3. The cosmetic composition of claim 1, wherein the organosiloxane emulsifier is a crosslinked organosiloxane emulsifier selected from the group consisting of dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer.

4. The cosmetic composition of claim 1, wherein the organosiloxane emulsifier is a linear organosiloxane emulsifier selected from the group consisting of cyclotetrasiloxane (and) cyclopentasiloxane (and) PEG/PPG-18 dimethicone; cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone.

5. The cosmetic composition of claim 1, wherein the (e) one or more thickeners are selected from the group consisting of xanthan gum, guar gum, biosaccharide gum, cellulose, acacia Seneca gum, sclerotium gum, agarose, pechtin, gellan gum, hyaluronic acid; and the polymeric thickeners are selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer.

6. The cosmetic composition of claim 1, further comprising:
    (f) one or more active agents selected from the group consisting of adenosine, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, and a coenzyme.

7. A ready to use cosmetic composition in the form of a water in oil emulsion comprising:
    (a) cholesterol;
    (b) non-crystallized ceramide-3 and non-crystallized ceramide-EOP,
    wherein the ratio of (a) to (b) is 1.8:1.0 to 3:1.0 and the total amount of the cholesterol, ceramide-3, and ceramide-EOP is from 4 wt. % to 9 wt. %, based on the total weight of the cosmetic composition;
    (c) dimethicone;
    (d) 0.5 wt. % to 10 wt. % of one or more organosiloxane emulsifiers; and
    (e) 0.1 wt. % to 10 wt. % of one or more thickeners;
    (f) adenosine; and
    (g) 45 wt. % to 65 wt. % of water, based on the total weight of the cosmetic composition.

8. A method for supporting natural lipid barrier function of skin comprising applying a composition of claim 1 to the skin.

9. A method for treating skin dryness comprising applying a composition of claim 1 to the skin.

10. A method for repairing skin damage due to photoaging comprising applying a composition of claim 1 to the skin.

11. A method for diminishing the appearance of wrinkles, dark spots, and uneven skin texture comprising applying a composition of claim 1 to the skin.

12. A process for manufacturing the cosmetic composition of claim 1 comprising:
    i. forming a fatty phase comprising:
        (a) the cholesterol;
        (b) the ceramide-3 and the ceramide-EOP;
        (c) the one or more silicone oils and the one or more hydrocarbon based oils;
        (d) the one or more organosiloxane emulsifiers; and
        (e) the one or more thickeners;
    ii. forming an aqueous phase comprising water and
        (f) the one or more active agents;
    iii. heating both the fatty phase and the aqueous phase to a temperature of at least 60° C.;
    iv. combining the fatty phase and the aqueous phase to form an emulsion while maintain both the fatty phase and the aqueous phase at a temperature of at least 60° C.; and
    v. cooling the emulsion.

* * * * *